(12) United States Patent
Chu et al.

(10) Patent No.: US 7,470,831 B1
(45) Date of Patent: Dec. 30, 2008

(54) GENETIC METHOD

(75) Inventors: Chengcai Chu, Gatersleben (DE); Nan Qu, Gatersleben (DE); Uwe Sonnewald, Gatersleben (DE); Ian Jepson, Bracknell (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/581,036

(22) PCT Filed: Dec. 10, 1998

(86) PCT No.: PCT/GB98/03687

§ 371 (c)(1),
(2), (4) Date: Aug. 8, 2000

(87) PCT Pub. No.: WO99/29881

PCT Pub. Date: Jun. 17, 1999

(30) Foreign Application Priority Data

Dec. 11, 1997 (EP) .................................. 97121829

(51) Int. Cl.
*C12N 15/29* (2006.01)
*C12N 15/52* (2006.01)
*C12N 15/82* (2006.01)
*A01H 5/00* (2006.01)

(52) U.S. Cl. ...................... 800/284; 800/287; 800/298; 800/317.2; 800/317.3

(58) Field of Classification Search ................. 800/278, 800/298; 536/23.1; 435/468
See application file for complete search history.

(56) References Cited

U.S. PATENT DOCUMENTS 5,436,394 A * 7/1995 Willmitzer et al. .......... 800/205

FOREIGN PATENT DOCUMENTS

| EP | 0 438 904 | 7/1991 |
| EP | 0 442 592 | 8/1991 |
| WO | 93/21334 | * 10/1993 |
| WO | WO 93/21334 | 10/1993 |
| WO | WO 97/07221 | 2/1997 |

OTHER PUBLICATIONS

Bussis et al., Solute accumulation and decareased photosynthesis in leaves of potato plants expressing yeast-derived invertase . . . , 1997, Planta, vol. 202 pp. 126-136.*
Sonnewald et al., Transgenic tobocco plants expressing yeast-derived invertase in either the cytosol, vacuole or apoplast: a powerful tool for . . . , 1991, The Plant Journal, vol. 1, No. 1, pp. 95-106.*
An ethanol inducible gene switch for plants used to manipulate carbon metabolism Caddick et al., 1996, Nature Biotechnology, vol. 16, pp. 177-180.

* cited by examiner

*Primary Examiner*—Russell Kallis
(74) *Attorney, Agent, or Firm*—Bruce Vrana

(57) ABSTRACT

The present invention describes a method of increasing plan yield. Also described are DNA constructs comprising DNA sequences coding for proteins involved in sucrose transport, metabolism and uptake operably linked to controllable promoter regions and plants transformed with said constructs. More particularly a method for the controlled production of said proteins resulting in an alteration in plant growth characteristics, flowering time and in yield is described.

9 Claims, 16 Drawing Sheets

Figure 1:
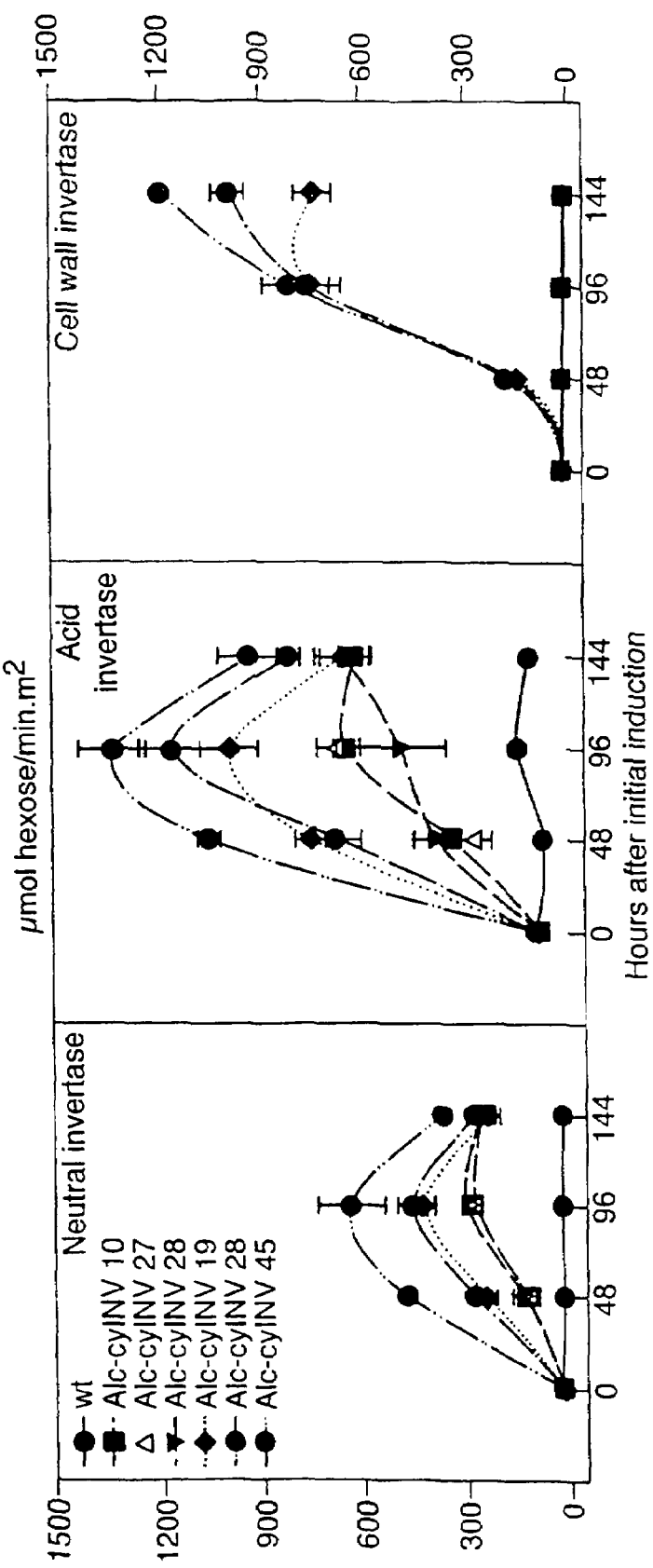

Fig.5.
A
B

Fig. 7.
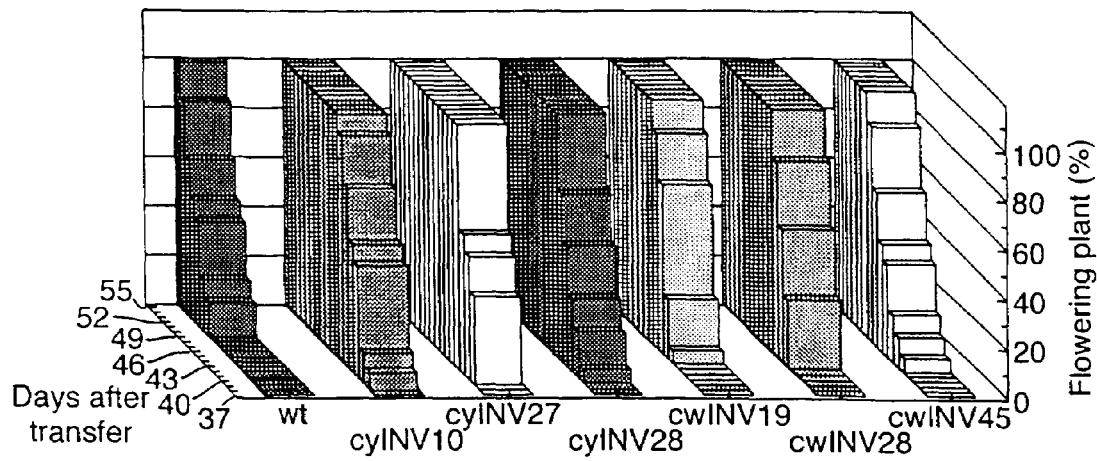
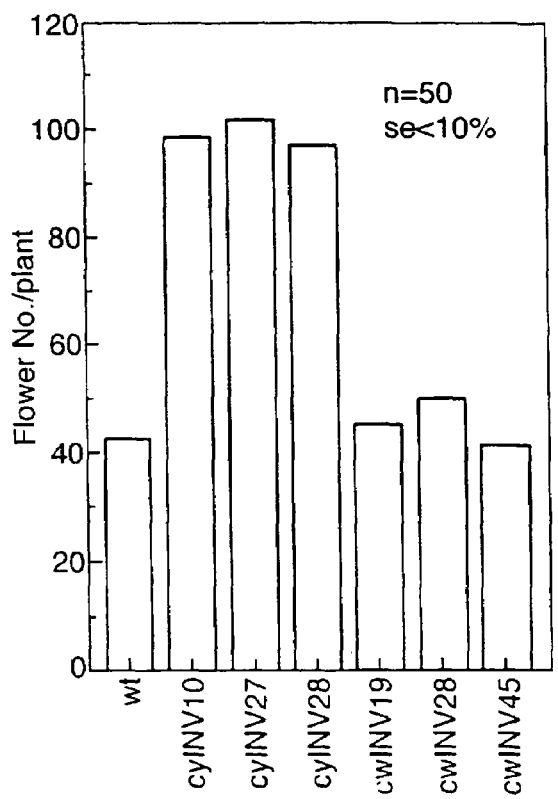

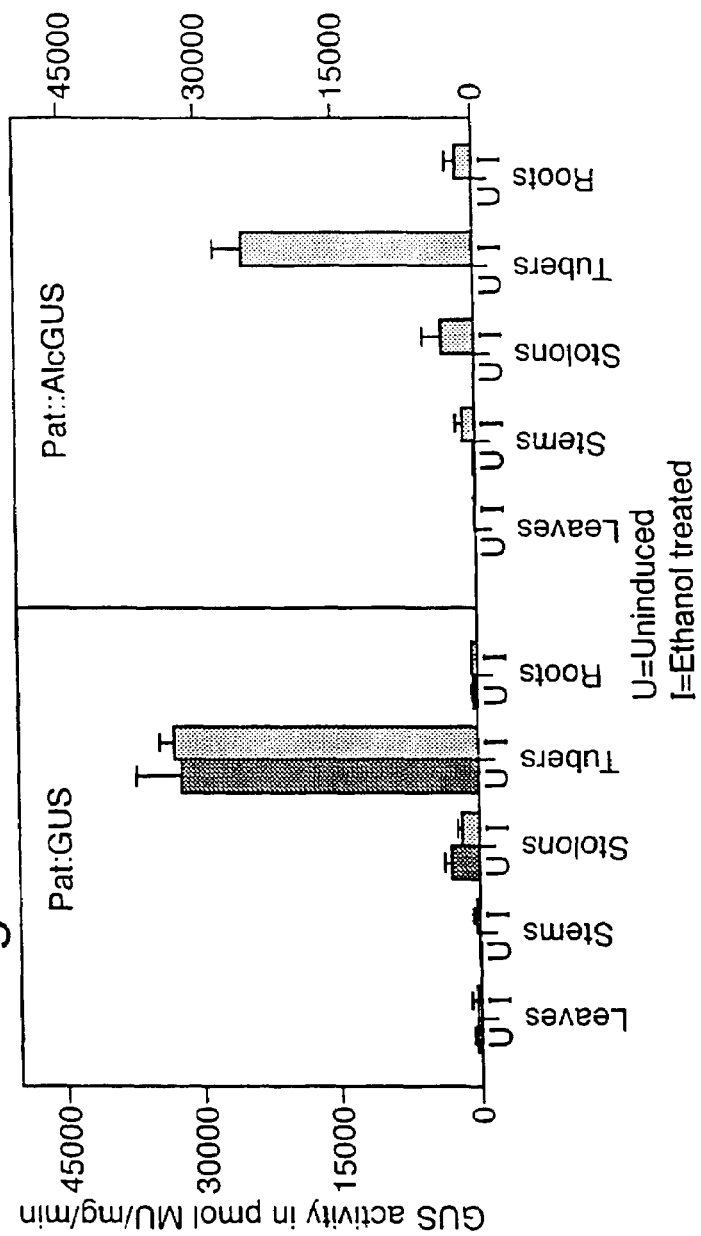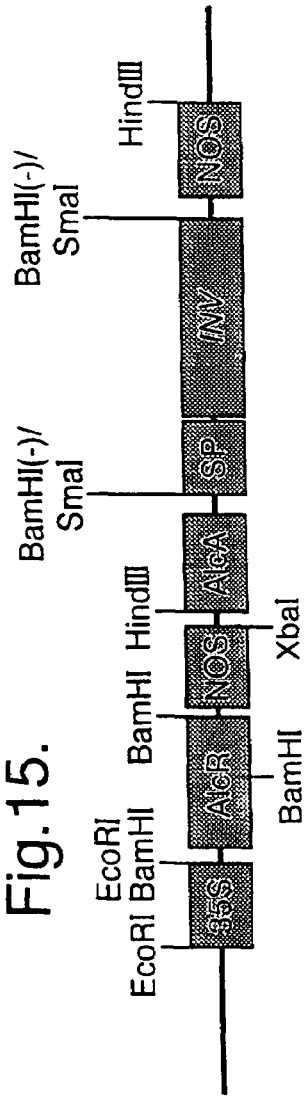
Fig. 14.
Fig. 15.

0 without induction
1 induced for 3 wks

GENETIC METHOD

The present invention relates to a method of increasing plant yield, to DNA constructs comprising DNA sequences coding for proteins involved in sucrose transport, metabolism and uptake operably linked to controllable promoter regions and to plants transformed with said constructs. More particularly the present invention relates to the controlled production of said proteins resulting in an alteration in plant growth characteristics, flowering time and in yield.

Photosynthesis is the major source of energy used to support biological processes in higher plants. The photosynthesising cells serve as important sources of photoassimilates or organic compounds produced in the plant by photosynthesis. Most fixed organic carbon is translocated from the source photosynthetic tissue to the non-photosynthetic organs which are known as the sink and this is the area in the plant where the translocated nutrients are either used or stored. The principal product of carbon fixation during the photosynthetic reaction is the disaccharide sucrose.

We have now found that by controlling the expression of DNA sequences coding for proteins involved in the transport, metabolism and uptake of sucrose using inducible promoter systems, it is possible to alter the sucrose levels in the plant in a controlled manner to produce the desired change in flowering and/or plant weight and/or height at the appropriate stage in plant growth whereby any effects deleterious to the plant are avoided and the overall yield of the plant is increased. The use of controllable promoter regions permits the expression of said DNA sequences to be regulated in a very precise way such that the optimal level of expression, the optimal time at which the DNA sequence is expressed and the optimal location in the plant may be determined.

According to a first aspect of the present invention there is provided a method of increasing the yield of a plant comprising transforming a plant with a DNA construct comprising one or more DNA sequence(s) coding for a protein involved in sucrose sensing, transport, metabolism and/or uptake operably linked to a controllable promoter region and optionally operably linked to a transcription terminator and controlling the level, time and spatial location of expression of said DNA sequence(s) from said controllable promoter region by application of an external chemical inducer whereby the yield of said transgenic plant is increased.

According to a preferred embodiment of the first aspect of the present invention there is provided a method of increasing the yield of a plant by selectively increasing the importation of fixed carbon into photosynthetically inactive sink tissues comprising transforming a plant with a DNA construct comprising one or more DNA sequence(s) coding for a protein involved in sucrose sensing, transport, metabolism and/or uptake operably linked to a controllable promoter region and optionally operably linked to a transcription terminator and controlling the level, time and spatial location of expression of said DNA sequence(s) from said controllable promoter region by application of an external chemical inducer whereby the transportation of fixed carbon from photosynthetically active source tissue to photosynthetically inactive sink tissue of said transgenic plant is selectively increased.

As used herein the term "source tissue" is used to denote those photosynthetically active tissues of the plant which are net exporters of fixed carbon and "sink tissue" denotes those photosynthetically inactive tissues of the plant which are net importers of fixed carbon.

It is economically and practically very desirable to be able to control both the ability to flower and the time of flowering of a plant. In some instances it may be desirable to synchronise flowering or to switch on flowering early or to manipulate flowering behaviour to suit the constraints imposed by growing in particular geographical areas. Generally an increase in the number of flowers is reflected in an increase in the eventual yield from the plant due to the increase in the number of seeds.

Similarly, an increase in the fresh weight of a plant as measured by an increase in leaf area results in an increase in yield due to the increase in the photosynthetic capacity of the plant.

Yield depends upon at least two parameters:—(i) sink induction and (ii) sink growth. Amongst other factors, sink induction can be stimulated by reducing the assimilate supply. This happens when invertase, for example, is induced in leaves. Sink growth depends upon the amount of assimilates allocated to the specific sink. This can be stimulated by sink-specific expression of the invertase. Since invertase activity negatively effects starch synthesis, chemical control of invertase expression is clearly advantageous over its constitutive expression.

An increase sink supply is likely to result in larger tubers when invertase expression is induced. The early flowering phenotype is, however, believed to be explained by a transient shortage of assimilate supply.

According to a second aspect of the present invention there is provided a method of controlling the flowering behaviour of a plant comprising transforming a plant with a DNA construct comprising one or more DNA sequence(s) coding for a protein involved in sucrose sensing, transport, metabolism and/or uptake operably linked to a controllable promoter region and optionally operably linked to a transcription terminator and controlling the level, time and spatial location of expression of said DNA sequence(s) from said controllable promoter region by application of an external chemical inducer whereby the flowering behaviour of said transgenic plant is altered.

The method of controlling flowering behaviour may be used to speed up the growth cycle of a plant such that more generations are produced.

The controllable promoter region in all aspects and embodiments of the present invention mentioned herein preferably comprises an inducible switch promoter system such as, for example, the alcA/alcR gene switch promoter system described in published International Patent Application No. WO 93/21334; the GST promoter as described in published International Patent Application Nos. WO 90/08826 and WO 93/031294; and the ecdysone switch system as described in published International Patent Application No. WO 96/37609 the teachings of which are incorporated herein by reference. Such promoter systems are herein referred to as "switch promoters". Switch promoter systems are particularly suitable for use in the method of the present invention since they allow the expression of DNA sequences to be switched on different parts of a transgenic plant at different times by means of sequential induction where the chemical inducer can be applied to the desired area of the plant at the desired stage of growth. For example, the switch chemical may be applied as a spray or vapour to all or part of the transgenic plant or as a root drench.

Examples of suitable switch chemicals are provided in the above references describing the switch promoter systems and are illustrated in the accompanying examples. The switch chemicals are desirably agriculturally acceptable chemicals.

Inducible promoter systems preferably include one or two component systems. Systems comprising more than two components are, however, also included. The switch system may be driven by a constitutive promoter or, preferably, by a tissue or organ specific promoter whereby the target gene is only switched on in a target tissue or organ.

The alcA/alcR switch promoter system is particularly preferred for use in all aspects of the present invention mentioned herein.

The alcA/alcR inducible promoter system is a two component system involving DNA sequences coding for the alcA promoter and the alcR protein, the expression of which is placed under the control of desired promoters. The alcR protein activates the alcA promoter in the presence of inducer and any gene placed under the control of the alcA promoter will therefore be expressed only in the presence of inducer. The promoter controlling expression of the alcR regulatory protein is preferably be a tissue or organ selective promoter, such as a leaf or tuber specific promoter, such that alcR is produced and alcA activated resulting in expression of the DNA sequence coding for the protein of interest only in selected parts of the plant such as for example the leaf, fruit, grain, endosperm or seed. When the method of the present invention is for use in cereal crops the expression of alcR is desirably controlled by a seed specific promoter; for use in grain the expression of alcR is desirably controlled by promoters associated with genes involved in starch synthesis or with seed storage proteins and for use with forage crops the expression of alcR is desirably controlled by leaf specific promoters. Examples of tissue or organ selective promoters are well known in the art and include for example seed specific promoters such as the Ltp2 promoter (Kalla et al, Plant J 6 (6) 849-60, (1994)), the zmGBS, the zmZ27, the osAGP and the osGT1 promoters (Russell and Fromm, Transgenic Res 1997, 6 (2) 157-68), the CMd promoter (Grosset et al, Plant Mol Biol 1997 34(2) 331-338), the glycinin A2B1a promoter, (Itoh et al Mol Gen Genet 1994 243(3) 353-357), the oleosin promoter from *Brassica napus* (Keddie et al Plant Molecular Biology 19 443-453, (1992)), the MatP6 oleosin promoter from cotton (Hughes et al, Plant Physiol (1993) 101 697-698), the oleosin promoter from *Arabidopsis* (Plant et al, Plant Mol. Biol. 25 193-205 (1994)), the zein promoter (Ottoboni et al Plant Mol Biol (1993) 21, 765-778), and fruit and organ specific promoters such as the patatin promoter (Rocha-Sosa et al EMBO J 8 23-30 1989), the promoter family associated with ribulose-1,5-bisphosphate carboxylase/oxygenase small subunit genes from tomato (Meier, Plant Physiol 107 (4) 1105-1118 (1995)), tomato rbcS3B and rbcS3C promoters (Carrasco Plant Mol Biol 21 (1) 1-15 (1993), the leaf promoter STL1 (Eckes et al Mol. Gen Genet 205 14-22 (1986)) and the rolC promoters.

According to a further preferred embodiment of the present invention there is provided a method of increasing plant yield comprising transforming a plant with a DNA construct comprising one or more DNA sequence(s) coding for a protein involved in sucrose sensing, transport, metabolism and/or uptake operably linked to the alcA/alcR controllable promoter region wherein the promoter controlling expression of the alcR regulatory protein is a tissue or organ specific promoter and is optionally operably linked to a transcription terminator and controlling the level, time and spatial location of expression of said DNA sequence(s) from said controllable promoter region by application of an external chemical inducer whereby the yield of said transgenic plant is increased.

Examples of DNA sequences which may be used in the method of the present invention to increase plant yield and to control flowering behaviour include those DNA sequences coding for proteins involved in the transport, uptake and subsequent metabolism of sucrose e.g. phosphofructokinase, invertase and hexokinase; in sucrose biosynthesis e.g. sucrose synthase, sucrose phosphate synthase and fructose-1,6-biphosphatase; in the transport of reserves during dormancy such as in phloem loading e.g. ATPase and sucrose and hexose transport proteins; in long distance phloem transport and in phloem unloading e.g. inorganic pyrophosphorylase (iPPase); in the utilisation of assimilates e.g. utilisation of sucrose-derived metabolites; in blocking starch synthesis (indirectly leading to increased sucrose levels); and invertase inhibitors.

The use of a controllable promoter region allows the production of the DNA sequence to be switched on in a controlled manner at the appropriate time in the growth cycle of the plant. We have unexpectedly found that the controlled expression of an invertase gene using the alcA/alcR switch promoter system leads to an increase in plant height, an increase in leaf size and to an increase of up to 10% in the fresh weight of a plant and accelerates the time at which the plants flower i.e the plants flower early.

According to a another preferred embodiment of the present invention there is therefore provided a method of increasing plant yield comprising transforming a plant with a DNA construct comprising a DNA sequence coding for an invertase operably linked to a controllable promoter region and optionally operably linked to a transcription terminator and controlling the level, time and spatial location of expression of said DNA sequence from said controllable promoter region by application of an external chemical inducer whereby the yield of said transgenic plant is increased.

According to yet another preferred embodiment of the present invention there is therefore provided a method of controlling the flowering behaviour of a plant comprising transforming a plant with a DNA construct comprising a DNA sequence coding for an invertase operably linked to a controllable promoter region and optionally operably linked to a transcription terminator and controlling the level, time and spatial location of expression of said DNA sequence from said controllable promoter region by application of an external chemical inducer whereby the flowering behaviour of said transgenic plant is altered.

The invertase may be derived from mammalian, bacterial, yeast, fungal or plant sources and may be different types such as acid invertase or neutral invertase. Invertase may be directed to different cellular locations such as the cell wall, the cytosol, the vacuole or apoplast by means of signal peptides (see Sonnewald et al. 1991 Plant J. 1:95-106).

According to a third aspect of the present invention there is provided a DNA construct comprising a DNA sequence coding for a protein involved in sucrose metabolism, uptake and/or transport operably linked to a controllable promoter region.

The DNA constructs according to the present invention may also optionally contain a transcription terminator sequence and/or a targeting sequence such that the invertase is targeted to a desired location within the plant. Examples of transcription terminators include the nopaline synthase transcription terminator and examples of suitable targeting sequences include for example signal sequences and vacuolar targeting sequences In a preferred embodiment of this aspect of the present invention the DNA sequence codes for invertase and the controllable promoter region is an inducible promoter region comprising the alcA/alcR switch promoter system.

Plant cells may be transformed with recombinant DNA constructs according to a variety of known methods such as with *Agrobacterium* Ti plasmids, electroporation, microinjection, microprojectile gun. The transformed cells may then be regenerated into whole plants in which the new nuclear material is stably incorporated into the genome. Some of the progeny of these primary transformants will inherit the recombinant DNA according to the present invention.

According to a fourth aspect of the present invention there is provided plant tissue transformed with a DNA construct comprising a DNA sequence coding for a protein involved in sucrose metabolism, uptake and or transport operably linked to a controllable promoter region and to the progeny of said plants.

Examples of suitable plants the yield of which may be increased and the flowering behaviour of which may be controlled according to the methods of the present invention and which may be transformed with DNA constructs according to the present invention include, for example, monocotyledonous and dicotyledonous plants such as field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage and onion; trees such as eucalyptus and poplar trees and cut flowers and ornamentals.

The method of the present invention may be particularly useful for improving the uniformity of banana fillings in a hand of bananas where commonly the banana fingers at the top of the hand fill first and split while those at the bottom are not full enough. According to the method of the present invention the sink strength of the bananas may be altered such that fixed carbon from those at the top of the hand may be drawn into those bananas at the bottom leading to a more uniform hand size.

The present invention is further illustrated only by way of example with reference to the following Examples and Figures in which:—

Figure 2:
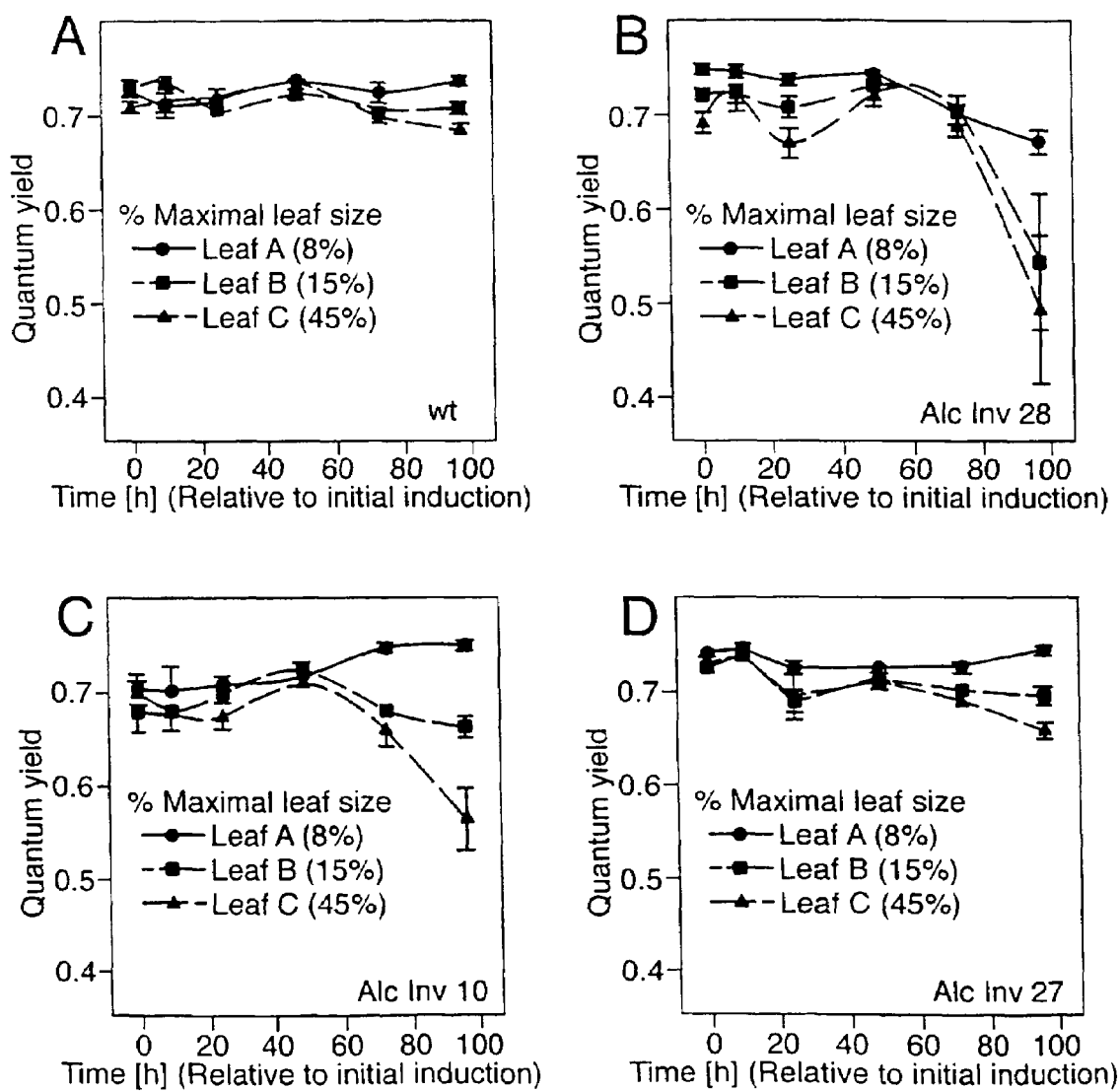

FIG. 1 shows invertase activity in source leaves of transgenic Alc:cytosolic invertase and Alc: cell wall invertase tobacco plants following ethanol induction FIG. 2 shows a graphical representation of quantum yield of wild type and transgenic tobacco plants at various time points after induction.

Figure 3:
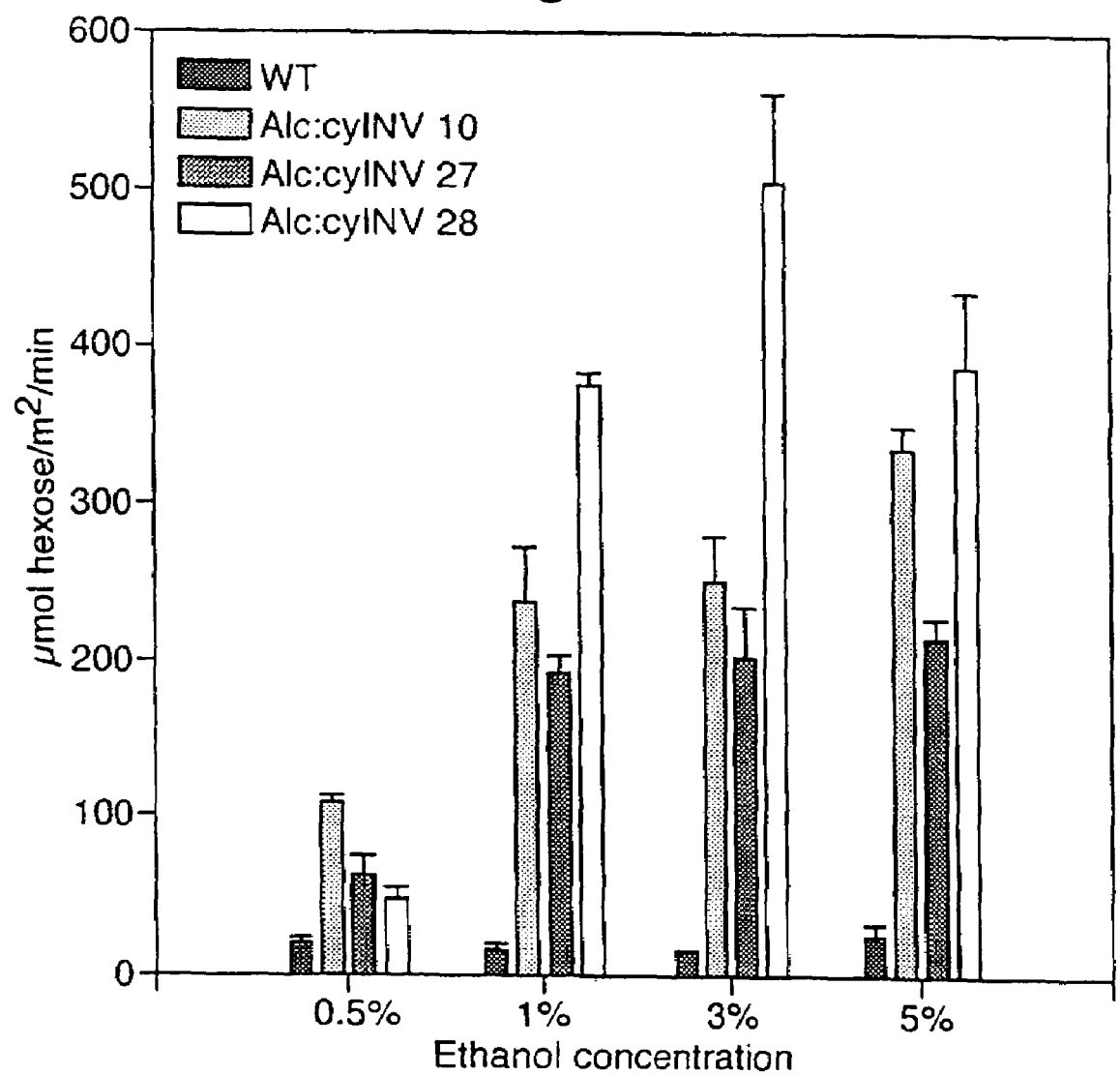
Figure 4:
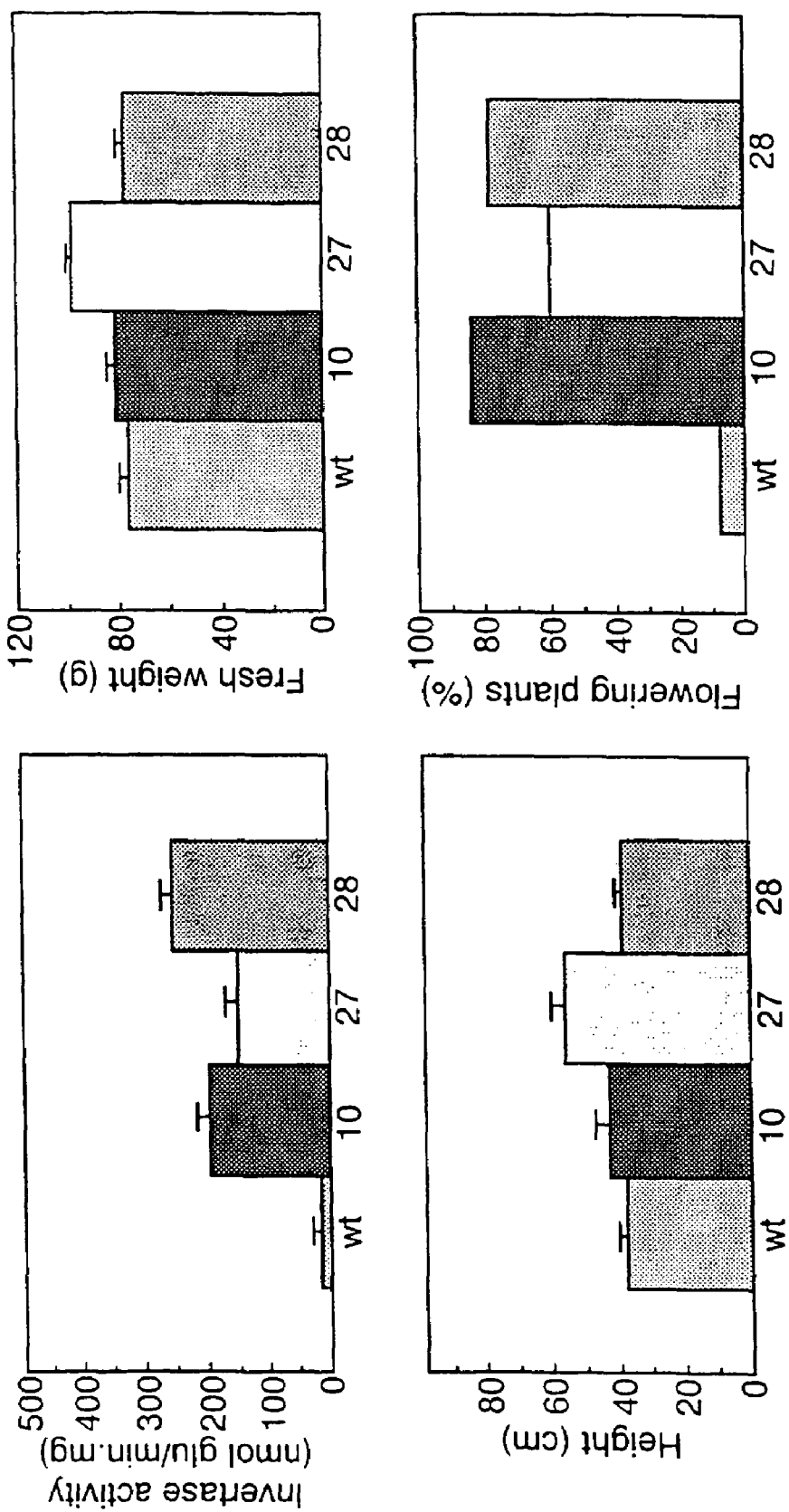

FIG. 3 shows a histogram analysis of invertase activity in transgenic plants at two different concentrations of ethanol (i.e. for wild type, alc:INV27, alc:INV10, alc:INV28 and 35ScytINV FIG. 4 shows histogram analysis of a) invertase activity; b) fresh weight; c) height and d) % flowering plants in wild type and transgenic tobacco plants induced by ethanol (i.e. wild type, alc:INV27, alc:INV10 and alc:INV28)

Figure 6:
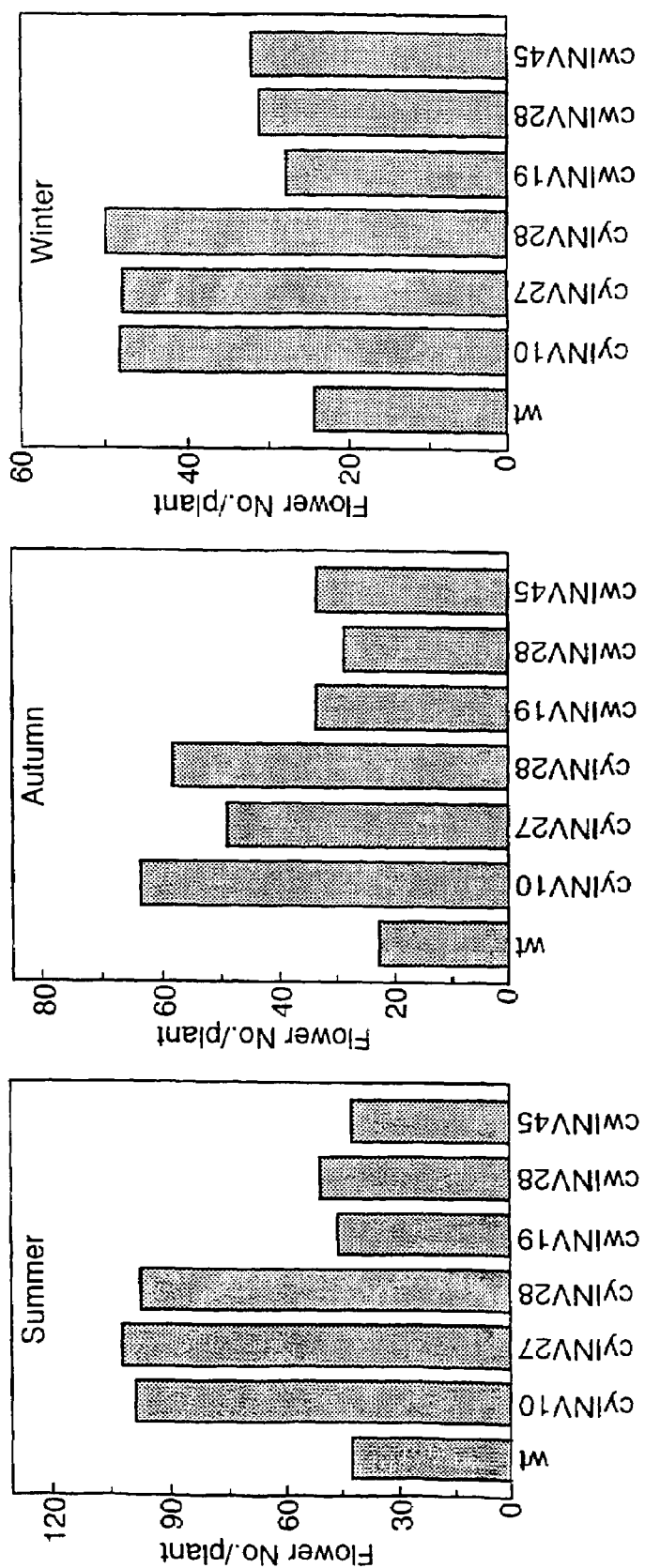
Figure 8:
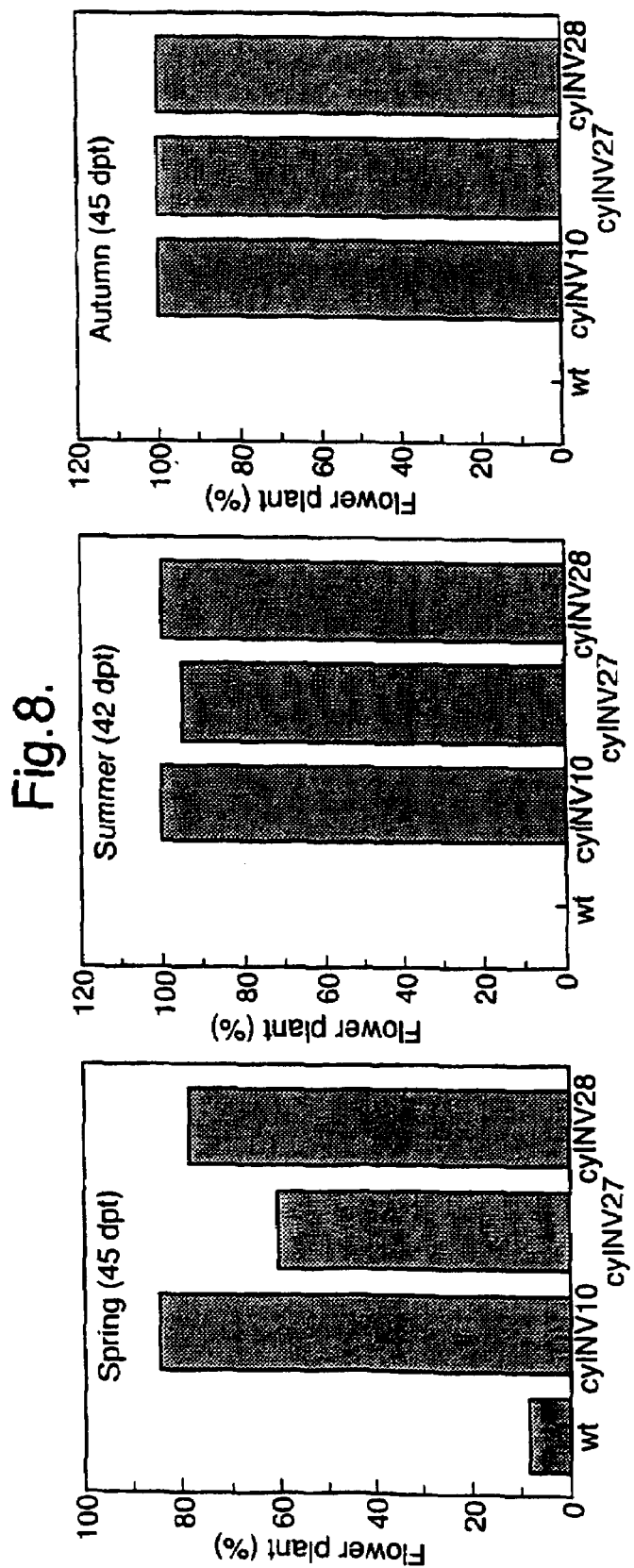
Figure 9:
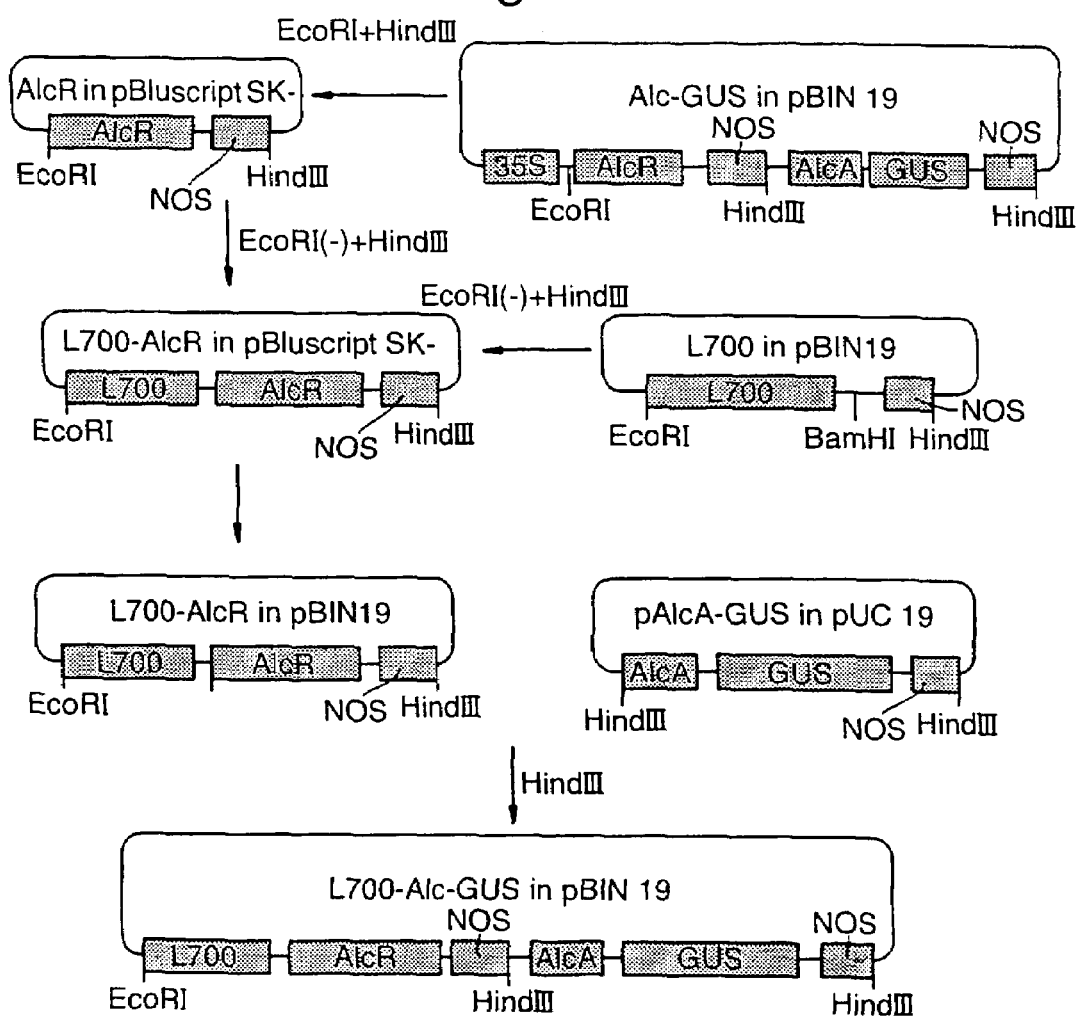
Figure 10:
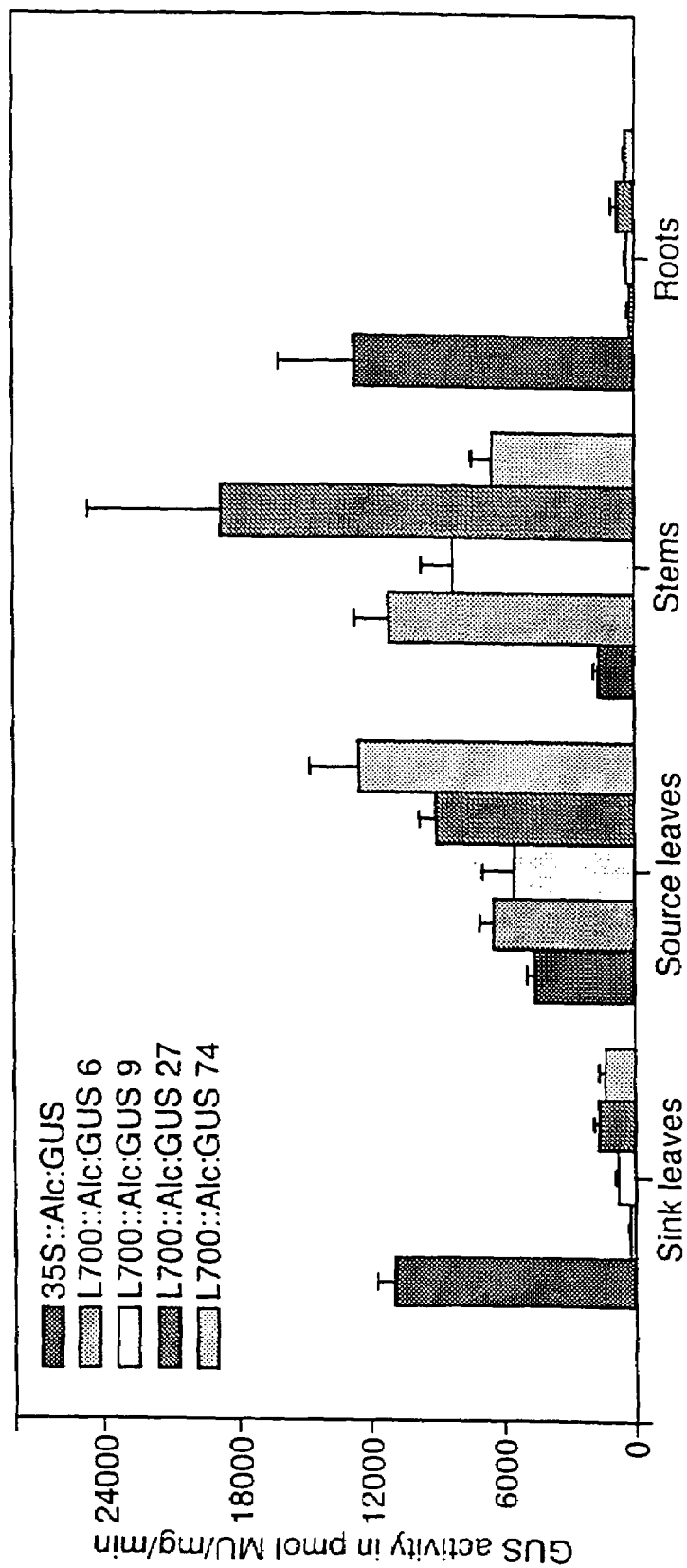
Figure 11:
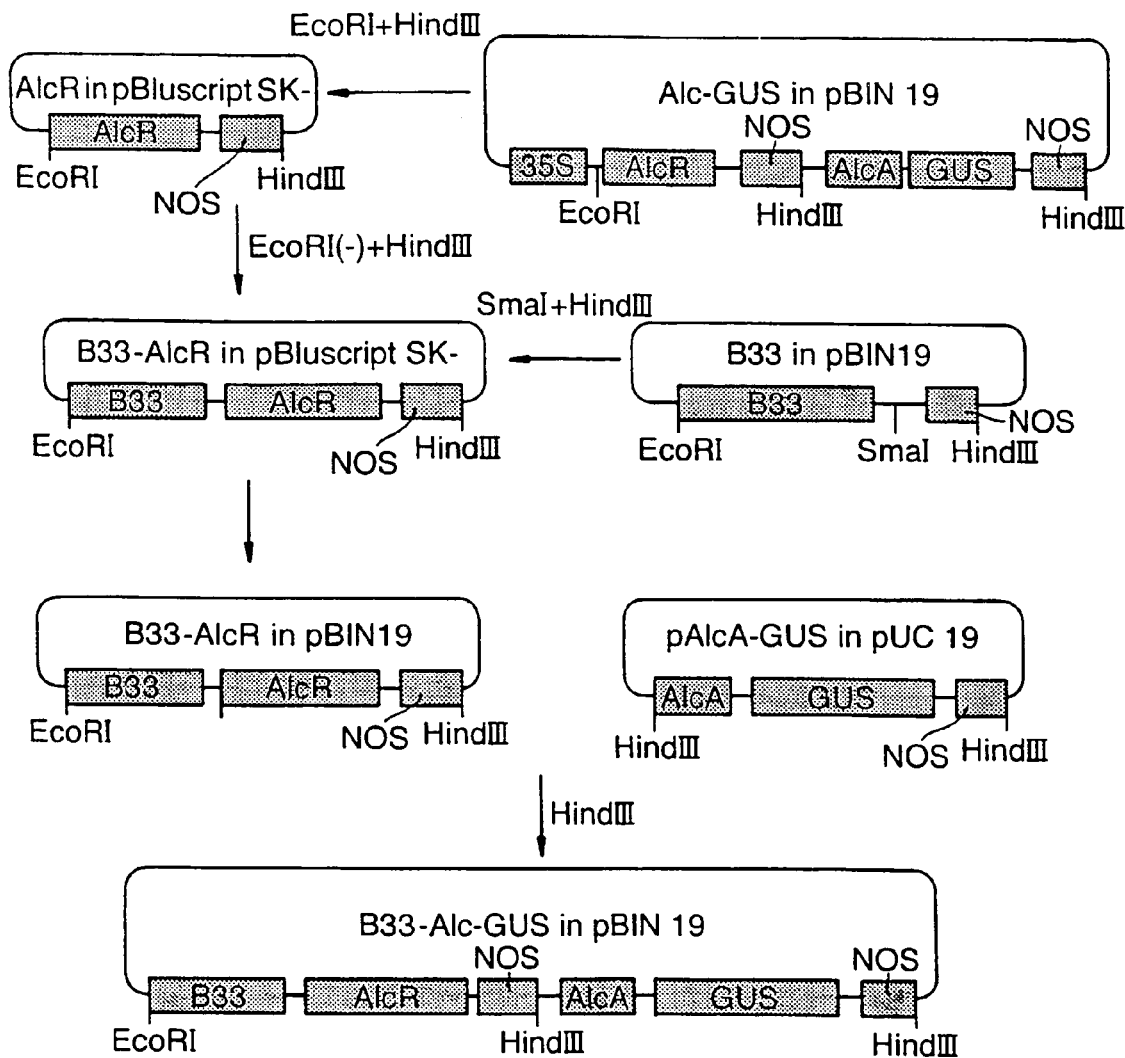
Figure 12:
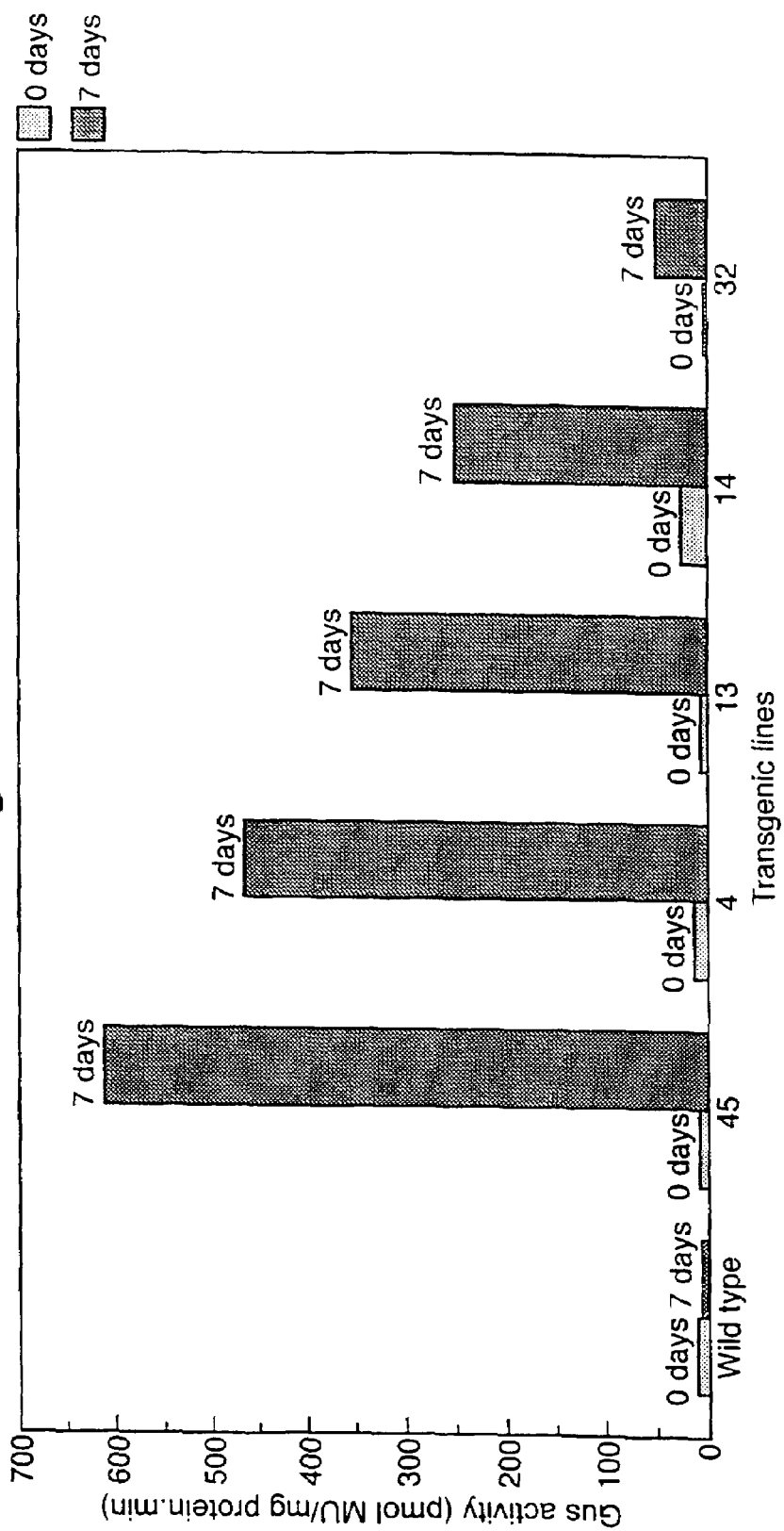
Figure 13:
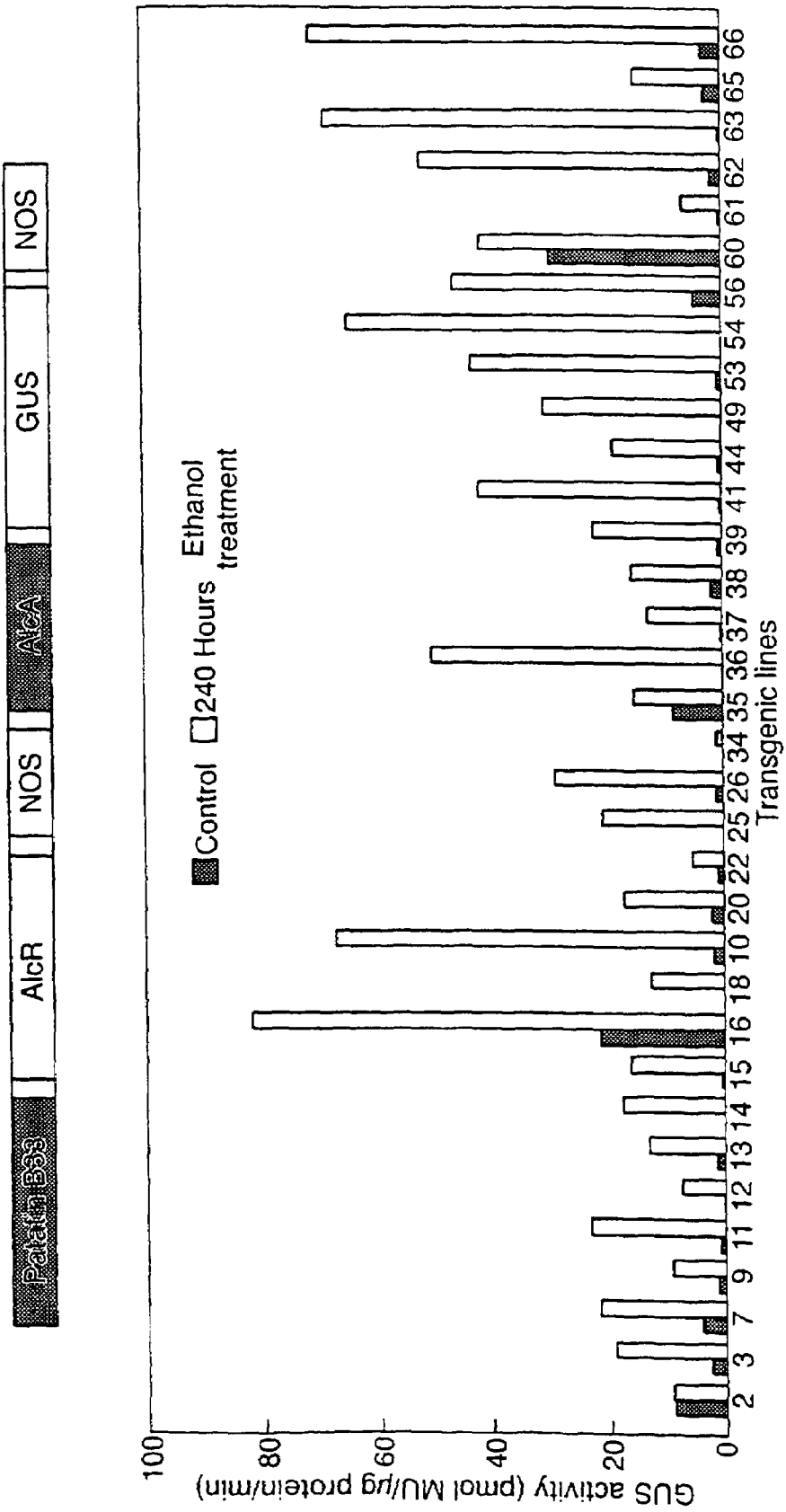
Figure 16:
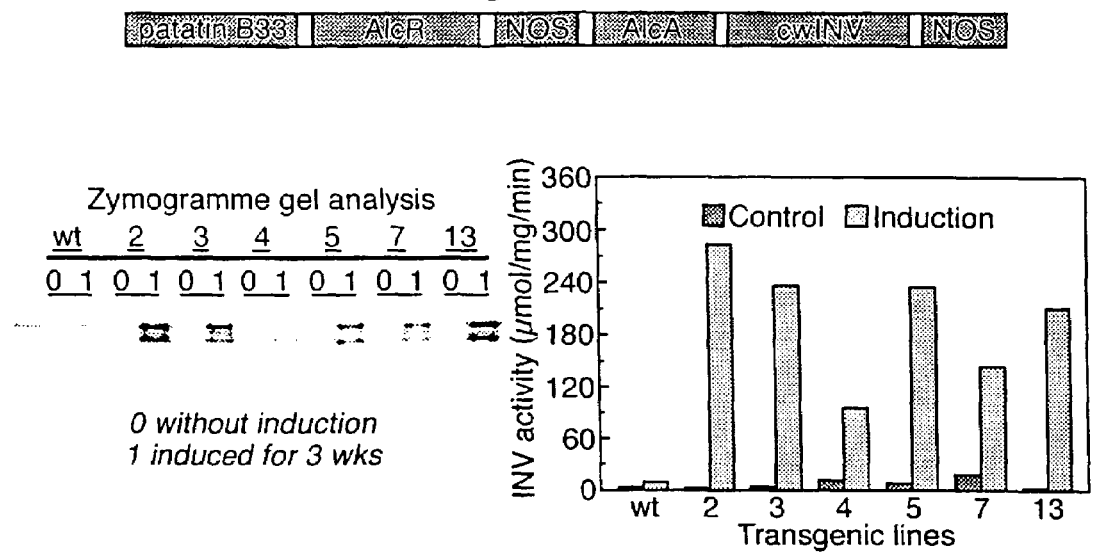
Figure 17:
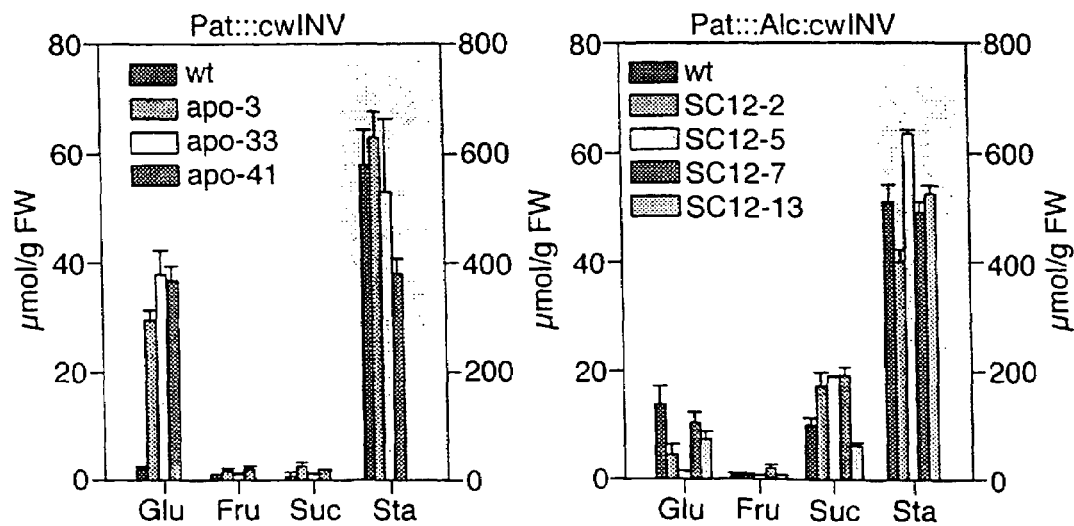
Figure 18:
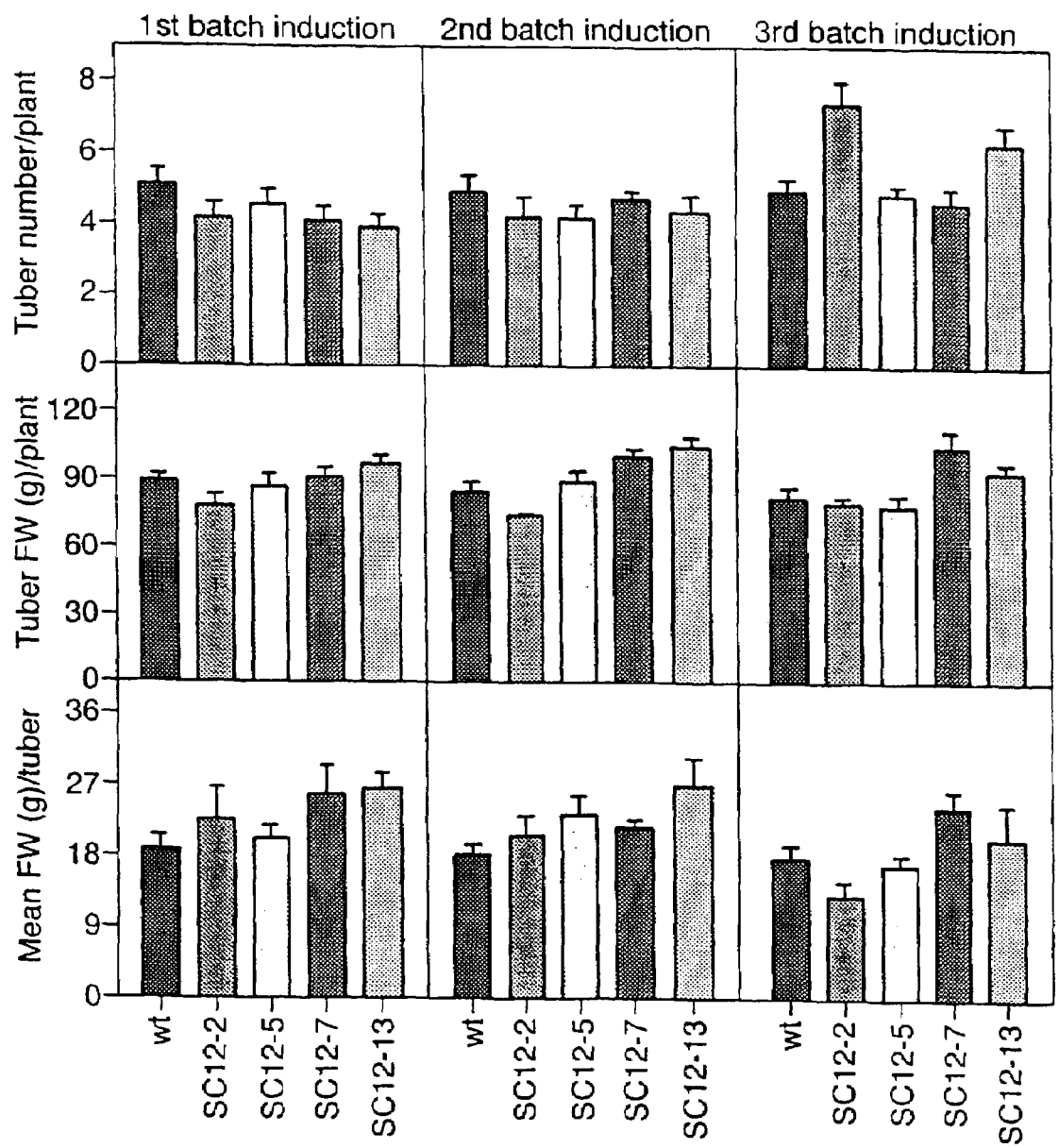

FIG. 5 shows a photograph of Alc invertase lines 27, 28, 10 and wild type A) no ethanol B) with ethanol FIG. 6 shows transient expression of invertase increased flower number in Alc:cyINV but not Alc:cwINV tobacco plants FIG. 7 shows the alteration of flowering behaviour in both Alc:cyINV and Alc:cwINV on expression of invertase FIG. 8 shows transient expression of invertase leading to early flowering in tobacco plants FIG. 9 shows the draft strategy for cloning an Alc GUS construct with an L700 promoter FIG. 10 shows organ specific expression of L700::Alc: GUS tobacco plants after 48 hours induction FIG. 11 shows the draft strategy for cloning an Alc GUS construct with patatin B33 promoter FIG. 12 shows a histogram analysis of GUS activity in wild type and transgenic potato tubers 0 and 7 days after induction FIG. 13 shows a histogram analysis of the levels of GUS activity observed in tubers of potato transformed with a patatin:alc:GUS construct induced with ethanol FIG. 14 shows tissue specific and ethanol inducible GUS expression in transgenic tobacco plants: tuber-specific expression of the alcR protein FIG. 15 shows the plasmid construction of patatin B33:: Alc:cwINV FIG. 16 shows invertase activity in patatin:Alc:cwINV potato tubers induced by ethanol FIG. 17 shows carbohydrate content in Pat::cwINV and Pat::Alc:cw INV potato growing tubers FIG. 18 shows increased potato tuber size resulting from early induction of apoplastic invertase expression

EXAMPLES

We have adapted the alc regulon of the ascomycete fungus *A. nidulans*, which has been well characterised (Pateman et al, Proc. Roy. Soc. London B 217, 243 (1983), Creaser et al, Biochem J. 225 449 (1985), Lockington et al, Mol. Microbiol 1, 275 (1987), Felenbok et al, Gene 73, 385 (1988), Felenbok et al, J. Biotechnol. 17, 11 (1991), Kulmberg et al, J. Biol. Chem 267, 21146 (1992), Kulmberg et al, Mol. Microbiol. 7 847, (1993), and Fillinger and Felenbok, Mol. Microbiol 20 475 (1996)). From classical genetics, it has been assumed that this is a self-contained genetic system that controls the cellular response to ethanol and other related chemicals. In *A. nidulans*, the alcA and aldA genes encode alcohol dehydrogenase I and aldehyde dehydrogenase, respectively (Pateman et al, Proc. Roy. Soc. London B 217, 243 (1983), Creaser et al, Biochem J. 225 449 (1985), Lockington et al, Mol. Microbiol 1, 275 (1987), Felenbok et al, Gene 73, 385 (1988), Felenbok et al, J. Biotechnol. 17, 11 (1991), Kulmberg et al, J. Biol. Chem 267, 21146 (1992), Kulmberg et al, Mol. Microbiol. 7 847, (1993), and Fillinger and Felenbok, Mol. Microbiol 20 475 (1996)). Both of these genes are regulated by the pathway-specific AlcR transcription factor (Pateman et al, Proc. Roy. Soc. London B 217, 243 (1983), Creaser et al, Biochem J. 225 449 (1985), Lockington et al, Mol. Microbiol 1, 275 (1987), Felenbok et al, Gene 73, 385 (1988), Felenbok et al, J. Biotechnol. 17, 11 (1991), Kulmberg et al, J. Biol. Chem 267, 21146 (1992), Kulmberg et al, Mol. Microbiol. 7 847, (1993), and Fillinger and Felenbok, Mol. Microbiol 20 475 (1996)). The AlcR protein binds to specific sites within the alcA promoter region and, as we demonstrate here, must respond directly to the inducer molecule (Pateman et al, Proc. Roy. Soc. London B 217, 243 (1983), Creaser et al, Biochem J. 225 449 (1985), Lockington et al, Mol. Microbiol 1, 275 (1987), Felenbok et al, Gene 73, 385 (1988), Felenbok et al, J. Biotechnol. 17, 11 (1991), Kulmberg et al, J. Biol. Chem 267, 21146 (1992), Kulmberg et al, Mol. Microbiol. 7 847, (1993), and Fillinger and Felenbok, Mol. Microbiol. 20 475 (1996)).

The alc regulon was considered suitable for a plant gene expression cassette for a number of reasons. First, the minimal regulon would include only the alcR gene and the alcA promoter. Second, the evolutionary divergence between *A. nidulans* and higher plants would make it unlikely that any plant homologues of the AlcR protein would activate the promoter: AlcR contains a zinc binuclear cluster like Gal4 (Pateman et al, Proc. Roy. Soc. London B 217, 243 (1983), Creaser et al, Biochem J. 225 449 (1985), Lockington et al, Mol. Microbiol 1, 275 (1987), Felenbok et al, Gene 73, 385 (1988), Felenbok et al, J. Biotechnol. 17, 11 (1991), Kulmberg et al, J. Biol. Chem 267, 21146 (1992), Kulmberg et al, Mol. Microbiol. 7 847, (1993), and Fillinger and Felenbok, Mol. Microbiol 20 475 (1996)) which has only been found in fungi so far. In addition, no other plant transcription factors were likely to cause interference at the alcA promoter. Third, the chemical inducers are relatively simple organic molecules with low phytotoxicity. Fourth, under normal growth conditions, the levels of natural inducers in the plant would be extremely low.

To test the efficacy of the system, plant expression cassettes were constructed. Construction of the alc derived gene constructs. p35S: alcR (A) utilised the 35S promoter from the Cauliflower Mosaic Virus to express AlcR protein from a cDNA. A partial alcR cDNA (provided by Felenbok) was excised from its Bluescript vector (Stratagene) by partial digestion with BamHI, ligated to BamHI digested pJR1 (Smith et al, Nature 334, 724 (1988)), a pUC derived vector containing the CaMV 35S promoter and the nos terminator, and transformed into *E. coli* XL-1 Blue (W. O. Bullock et al. BioTechniques 5, 376 (1987); J. Sambrook et al., Molecular cloning: A laboratory manual, edn. (Cold Spring Harbor Laboratory Press, Cold Spring Harbor, N.Y., 1989). The alcA reporter cassette, palcA: CAT (B), was constructed by digestion of pCaMVCN with HindIII and BamHI to remove the promoter. (pCaMVCN is a plant expression vector available from Pharmacia. It is a pUC—derived vector in which the CaMV 35S promoter expresses the bacterial CAT gene. The terminator is from the nos gene of *A. tumefaciens*.) Since the TATA boxes of the AlcA and 35S promoters were identical (5'TCTATATAA3'), recombinant PCR was used to amplify and fuse both fragments through this site (Higuchi in PCR Protocols, M. A. Innis et al, eds (Academic Press, San Diego (1990) p 177-183). The alcA PCR product extended from the TATA box for 246 bp upstream, and included ALCR binding sites (Pateman et al, Proc. Roy. Soc. London B 217, 243 (1983), Creaser et al, Biochem J. 225 449 (1985), Lockington et al, Mol. Microbiol 1, 275 (1987), Felenbok et al, Gene 73, 385 (1988), Felenbok et al, J. Biotechnol. 17, 11 (1991), Kulmberg et al, J. Biol. Chem 267, 21146 (1992), Kulmberg et al, Mol. Microbiol. 7 847, (1993), and Fillinger and Felenbok, Mol. Microbiol 20 475 (1996)). The 35S PCR product included the common TATA box sequence and extended downstream to span a convenient BamHI site for subsequent cloning; the minimal 35S promoter is known not to be expressed in plants (It has been shown that a minimal 35S promoter containing only those sequences between positions −46 and +5 lacks the ability to initiate transcription (Odell et al Nature 346, 390 (1985); Hilson et al, Plant Cell 2 651 (1990) Schena et al Proc. Natl. Acad Sci USA 88, 10421 (1991). It is reasonable to expect that fusion of palcA through the TATA sequence (positions −31 to +1) would also be inactive.) The resultant product was digested with HindIII and BamHI, and ligated into the promoterless pCaMVCN. After transformation into *E. coli*, colonies were screened to select a plasmid which contained the appropriate palcA:35S fusion promoter, and the HindIII and BamHI fragment was sequenced to ensure that there were no PCR errors. The palcA::Inv construct was obtained by deletion of the GUS reporter gene from plasmid palcA:GUS and insertion of the truncated yeast suc2 gene isolated from plasmid rolC-suc2 as a BamHI fragment (Lerchl et al (1995) Plant Cell 7, 259 (1995). For plant transformation, the p35S:alcR cassette was cloned into a Bin19-derived vector (Deblacre et al, Nucleic Acids Res. 13, 4777 (1985), together with either the palcA: CAT or the palcA:Inv construct, transformed into *A. tumefaciens* (Holsters et al. Mol. Gen. Genet. 163, 181 (1978); Vervliet et al. J. Gen. Virol 26, 33 (1975)). Tobacco transforming using *Agrobacterium*-mediated gene transfer was carried out as described previously (Rosahl et al EMBO J. 6 1159 (1987) and Komari et al Plant Science 60 223 (1989)).

The bacterial chloramphenicol acetyltransferase gene (CAT) was used as a reporter gene so that levels of expressed protein could be determined using ELISA. When transformed into *A. nidulans* (Ballance and Turner Gene 36, 321 (1983); Campbell et al). Curr. Genet. (1989), the palcA:CAT construct showed inducible CAT activity, and p35S:alcR restored the wild-type phenotype to an alcR mutant (data not shown). Transient assays (Callis et al Genes and Develop 1 1183 (1987)) in maize protoplasts revealed that the AlcR protein could stimulate the transcription from the alcA promoter in plant cells and that expression was at least partially regulated by ethanol (data not shown).

After *Agrobacterium tumefaciens* mediated transformation a transgenic tobacco plant carrying the p35S:alcR and palcA:CAT cassettes was selected and tested by PCR for the presence of both cassettes (data not shown). This plant was selfed, and the seedling progeny assayed for both the selectable marker and CAT expression. The construct segregated among the progeny in a Mendelian ratio (1 non-transgenic:2 hemizygous:1 homozygous) consistent with a single copy of the cassettes in the parent plant (data not shown).

A selected seedling was grown to maturity to produce a homozygous line. Seedlings of this plant were tested for CAT protein in comparison to seedlings of a similar plant transformed with a construct which expressed CAT from the constitutive high activity CaMV 35S promoter (Table 1). The homozygous palc:CAT seedlings had barely detectable CAT protein in the absence of induction, but had 39% of the CAT activity of the untreated p35S:CAT seedlings and 55% relative to the ethanol-treated p35S:CAT seedlings. Thus, ethanol treatment of p35S:CAT seedlings resulted in a reduction [29%] in CAT protein levels relative to the untreated control.

While the induced levels of expression were lower than that from the 35S promoter, the negligible basal activity indicated its suitability for the manipulation of carbon metabolism. A range of inducible invertase vectors were made by replacing the CAT reporter gene with the truncated yeast suc2 GENE 100, a cytosolic yeast derived invertase. In this regard, the Bam HI fragment isolated from plasmid RolC::Suc2 (Lerchl et al, 1995, Plant Cell 7, 259-270) was used to replace the reporter gene. The fragment contained nucleotides 848 to 2393 of the yeast such2 gene (Accession number Y01311) and encoded an invertase protein without a signal peptide. Invertases from other sources and of different type, such as acid invertase, or other targeted invertases were also made using transit peptide invertase combinations described in Sonnewald et al., 1992, Plant J. 1:95-106 which may be expressed in the cell wall or subcellular locations such as the vacuole or the apoplast (details of cloning are described in Caddick et al. Nature Biotech, Vol 16, February 1998 page 177 and in Lerchl J. et al. 1995, Plant Cell 7: 250-270 and Sonnewald et al.). Transgenic tobacco plants carrying palcA: cyInv were isolated (Tobacco (*Nicotiana tabacum* cv. Samsun NN) transformation using *Agrobacterium*-mediated gene transfer was carried out as described by Rosahl et al. EMBO J. 13, 1 (1987)). After screening about 100 independent kanamycin resistant regenerants for ethanol inducible invertase activity, 23 invertase expressing plants could be identified. Of 23 plants exhibiting inducible invertase activity, three lines [10, 27 and 28] were selected for more detailed analysis. To this end, plants were multiplied in tissue culture and 50 plants of each line were transferred into the greenhouse. After 21 days of growth in 2 L pots, initial induction was carried out via root drenching with 100 ml of a 1% ethanol solution (v/v). To accelerate the ethanol response, induction was repeated at 48 and 72 hours after the initial root drench. To assay invertase activity, samples were taken at 0, 1, 6, 24, 48, 72 and 96 hours after the initial induction (see FIG. 1). Elevated invertase activity was measurable in all three transgenic lines already 6 hours after the first addition of ethanol. Invertase activity increased steadily reaching a plateau 96 hours after the initial root drenching in two lines [10 and 27], while in the third [28], it was still increasing.

Phenotypic modification started 72 hours after ethanol induction and was strongest after 96 hours. The final phenotype was identical to the previously published results using the 35S CaMV promoter to drive the expression of cytosolic yeast invertase (Sonnewald et al Plant J. 1, 95 (1991)). Development of this phenotype followed maximal invertase activity and was most severe in transformant 28. Photosynthesis fluorescence measurements were used to monitor changes of quantum yield (Schreiber et al, in Ecophysiology of Photosynthesis Vol. 100, Schuize and Caldwell, Eds (Springer Verlag, Berlin, 1994), pp 49-70.) of all three transformant lines in vivo throughout the induction experiment. During the course of ethanol treatment, quantum yield did not change markedly in the youngest leaves (leaves A 8% of maximal leaf area). However, coinciding with the developing visual phenotype quantum yield decreased significantly ($p>0.05$) in leaves B (15% of max) and C (45% of max) of plants from line 10 and 28 starting 72 hours after the initial induction and developing further until the final time point at 96 h.

FIG. 2 shows evidence for a reduced rate of photosynthesis following the increase of invertase activity in transgenic tobacco plants as determined by quantum yield measurements. Fluorescence measurements were used to monitor changes in photosynthetic parameters during induction of invertase activity using the PAM-2000 instrument (Walz, Effeltrich, Germany). Quantum use efficiency (quantum yield) of photosystem II (PSII) was measured by applying a saturating light beam on light adapted leaves of wildtype and transformed plants (palc:Inv). Before each measurement, it was verified that the saturating pulse had reached a plateau to allow an accurate determination of Fm'. The intensities of the measuring and saturating light beam were adjusted to reach a FO' value close to 0.4. Measurements were conducted on different leaves having reached 8% (A), 15% (B), or 45% (C) of maximal leaf area of five plants of each genotype at the indicated time points.

Quantum yield of three succeeding light adapted leaves (leaf A-C) starting from the top of the plant was measured using a PAM-2000 instrument at the time points indicated. Values given are the means +−SE (n=5). For plants of line 28, quantum yield was reduced by 23% ($p<0.05$) and 27% ($p<0.05$) and for plants of line 10 only by 6% and 17% ($p<0.05$), respectively. Due to heterogeneity of the developing phenotype between individual plants from each genotype, standard errors were higher in the affected leaves (B and C).

The table below shows CAT activity levels in transgenic tobacco. Individual seedlings from a homozygous transgenic tobacco line carrying the CAT gene expressed from the alcA promoter were compared with those from a similar line transformed with p35S:CAT. Plants were grown on liquid media until 4 weeks old, and showed four true leaves (seed progeny of tobacco plants were grown by sowing seeds directly onto a 2 cm layer of sterile alcathene beads (5 mm diameter) floating on a sterile solution of 0.5% (w/v) Miracle Gro in 500 ml beakers. The beakers were covered with a perforated plastic bag and incubated at 25° C. under high intensity lights in a growth room). Induction was achieved by the addition of 0.1% ethanol to the growth medium for 120 h. The induction medium was replaced at 58 h to maintain ethanol concentrations. One leaf was taken prior to induction, and one leaf after induction. CAT ELISA (Boehringer Mannheim) was performed on crude cell extracts; total protein was determined as described previously (Bradford, Anal Biochem 72: 243 (1976). All values are ng CAT protein per mg total protein, and represent the mean of nine individual replicates±one standard deviation.

| Line | Untreated | Ethanol-induced |
| --- | --- | --- |
| palcA:CAT | 0.36 + 0.43 | 30.37 + 3.91 |
| p35S:CAT | 78.08 + 30.44 | 55.46 + 10.85 |

It can be seen from FIG. 3 that the invertase activity in transgenic plants is dose-dependent and that the activity at 5% ethanol is significantly greater than it is at 1% ethanol. It is, therefore, possible to regulate invertase in a dose dependent manner using the Alc switch.

In order to see the impact of inducible cytosolic invertase expression on plant growth and flowering time, tobacco plants were vegetatively propagated in tissue culture (FIG. 4). Subsequently 50 plantlets each genotype were transferred into the greenhouse. In FIG. 4, wt denotes a wild type transgenic control and lines 10, 27 and 28 represent 50 cloning propagated independent lines containing 35S:alc A:suc 2. Three weeks after transfer, plants were induced with 100 ml 1% (v/v) via root drenching. Induction was repeated three times (0, 48 and 72 hours). In particular, FIG. 4a) shows cytosolic neutral invertase activity (suc 2) measured 96 hours after initial induction, FIG. 4b) shows fresh weight of the above ground biomass 45 days after transfer and FIG. 4c) shows plant height 45 days after transfer. FIG. 4d) shows the percentage of plants which were flowering when scored 45 days after transfer.

To show the impact of ethanol inducible cytosolic invertase on plant height and flowering, plants were propagated in tissue culture and transferred into the greenhouse (FIG. 5). Three weeks after transfer one half of the plants were induced with ethanol as described for FIG. 4. The second half of the plants was transferred into a second greenhouse without any ethanol treatment. The upper panel (A) shows four tobacco plants 7 weeks after transfer from tissue culture without ethanol induction. The lower panel (B) shows the same genotypes 4 weeks after initial ethanol induction. From left to right the following genotypes are shown: 1, line 27; 2, line 10; 3, line 28; line 4, untransformed control. The early flower phenotype was consistently found in all experiments.

In order to show that inducible invertase expression leads to an increased flower number per plant, 25 plants of each genotype (wt, cyt inv10, cy inv 27, cyt inv 28, cw inv 19, cw inv 28 and cw inv 45) were propagated in tissue culture and transferred into the greenhouse (FIG. 6). Three weeks after transfer plants were induced as described above. The total number of flowers produced each plant was determined at the end of the growing period.

As can be seen from FIG. 7, transgenic plants expressing inducible invertase have accelerated flower induction. 25 plants of each genotype were propagated in tissue culture and transferred into the greenhouse. Three weeks after transfer plants were induced as described above. Subsequently, flower formation was followed throughout the growing period. Plants were classified as flowering when the first flower bud was open. Values are given in [%] flowering plants per total number of plants (n=25).

As can be seen from FIG. 8, the early flower phenotype is reproducible at different growing seasons by means of transient expression of invertase. In this regard, 50 (spring) and 25 (summer and autumn) plants of each genotype were used for the individual experiments, respectively. After propagation, plants were transferred into the greenhouse and induction started three weeks after transfer as described above. At the indicated time after transfer (dpt, days after transfer) plants with open flower buds were counted. Values are given in [%] flowering plants per total number of plants.

Preparation of Plasmid pSTLS1:AlcR:AlcA:GUS (SC08)

To obtain plasmid SC08, the EcoRI/HindIII fragment of plasmid AlcR/A GUS containing the AlcR coding region and the NOS terminator was subcloned into pBluescript SK-yielding plasmid pAlcR. Subsequently, plasmid pAlcR was digested with EcoRI, blunt ended with DNA polymerase (Klenow fragment), further restricted with HindIII and ligated into plasmid pBINSTSL1 after BamHI digestion, Klenow treatment and Hind III digestion yielding plasmid pBIN:STSL1:AlcR. Plasmid pBINSTSL1 consists of the STSL1 promoter corresponding to nucleotide +1 to +1585 of the published sequence of the STSL1 gene from potato (Eckes et al (1986) Mol. Gen. Genet. 205 14-22) and the OCS (octopine synthase) terminator. The final construct SC08 was obtained by ligating the HindIII fragment from plasmid AlcR/A GUS containing the AlcA promoter, the GUS coding region and the NOS terminator into the HindIII digested vector pBIN:STSL1:AlcR. The strategy for cloning an Alc GUS construct with the L700 promoter is shown in FIG. 9.

The tissue specific and ethanol inducible GUS expression in transgenic tobacco plants i.e. leaf/stem-specific control of the alcR protein is shown in FIG. 10. Trangenic tobacco plants expressing the GUS reporter gene under control of the ethanol inducible system were propagated in tissue culture and transferred into the greenhouse. Three weeks after transfer plants were induced via root drenching using 100 ml 1% ethanol. 48 hours after induction tissue samples were harvested and GUS activity determined in protein extracts:—sink leaves, <3 cm; source leaves. 35S::Alc:GUS, root and stem expression of the alcR protein under control of the 35S CaMV promoter was used as a constitutive control. L700::Alc:GUS expression of the alcR protein under control of the leaf/stem-specific ST-LS1 promoter from potato in 4 independent transgenic lines (6, 9, 27 and 74) were also used.

Preparation of Plasmid B33:AlcR:AlcA:GUS (SC09)

To obtain plasmid SC09, the EcoRI/HindIII fragment of plasmid AlcR/A GUS containing the AlcR coding region and the NOS terminator was subcloned into pBluescriptSK– yielding plasmid pAlcR. Subsequently, plasmid pAlcR was digested with EcoRI, blunt ended with DNA polymerase (Klenow fragment), further restricted with HindIII and ligated into the SmaI/HindIII digested plasmid pBIN:B33AlcR. Plasmid pBINB33 consists of the patatin class I promoter, corresponding to nucleotide –1512 to +14 of the patatin gene B33 (Rocha-Sosa et al. (1989) EBO J. 8 23-29) and the OCS terminator. The final construct SC09 was obtained by ligating the HindIII fragment from plasmid AlcR/A GUS containing the AlcA promoter, the GUS coding region and the NOS terminator into the HindIII digested vector pBIN:B33AlcR. A strategy for cloning an Alc GUS construct with a patatin B33 promoter is shown in FIG. 11.

Alc R Patatin alc A GUS Vector pSC09 (B33-alc GUS in Bin 19) was transformed directly into *Agrobacterium tumefaciens* strain C58C1:pGV2260 using the protocol described by Hofgen and Willmitzer (1988). Potato (var Solara) transformation using *Agrobacterium*-mediated gene transfer was performed as described by Roscha-Sosa et al (1989). Transgenic plants were duplicated in tissue culture and one set transferred to the glasshouse following root formation. Plants were grown to maturity and tubers harvested. For each independent transformant tuber, samples were taken for GUS analysis in the absence of ethanol treatment. Additional tubers were transferred to perspex boxes containing a pot of 1% ethanol. Following 7 days of ethanol vapour treatment, tubers were harvested and assayed for GUS activity. FIG. 13 demonstrates that high levels of transgene expression is observed in the tubers following ethanol treatment.

Transgenic potato plants expressing the GUS reporter gene under control of the ethanol inducible system were propagated in tissue culture and transferred into the greenhouse. Two months after transfer, plants were induced via root drenching using 100 ml 1% ethanol. 48 hours after induction, tissue samples were harvested and GUS activity determined in protein extracts:—leaves, stems and tubers >5 g. Pat:GUS expression of the GUS reporter gene under control of the class I patatin promoter B33 acted as a control. Pat::Alc:GUS expression of the alcR protein under control of the tuber-specific B33 promoter from potato was also used. The activity is given in pmol MU/mg/min. FIG. 14 shows tissue specific and ethanol inducible GUS expression in tobacco plants by tuber-specific expression of the alcR protein.

The EcoRI and HindIII fragment containing transactivator AlcR gene and NOS terminator was from plasmid 35S:AlcR-AlcA:GUS (35S-Alc:GUS, Plant Journal 1998, 16 (1) 127-132) and subsequently subcloned into Bluescript SK– (STRATAGENE) (AlcR in SK–). The plasmid AlcR in SK– was digested with EcoRI and filling-in with Klenow fragment to make it blunt and further cut with HindIII. This EcoRI(–)-HindIII fragment was cloned into binary vector Bin-B33 cut by SmaII and HindIII resulting in the plasmid patatin B33:AlcR in pBIN19. The PCR product of yeast invertase with protein inhibitor II signal peptide (SP) sequence (von Schaewen et al. (1990) EMBO J. 9. 3033-3044) was cloned into pGEM-T vector by primer K83 and K84 which containing the SmaII site. The SmaII fragment was subcloned into pUC-AlcA plasmid via BamHI site which was blunted by T4 DNA polymerase. The orientation was checked by combining Asp718 and EcoRI, and also with XbaI. The correct orientation plasmid was subsequently subcloned into patatin B33:AlcR in pBIN19 resulting the final plasmid patatin B33:AlcR-AlcA:cwINV in BIN19 (patatin B33::Alc:cwINV). The construction of the plasmid is shown in FIG. 15.

Transgenic potato plants were propagated in tissue culture and subsequently transferred into the greenhouse. After tuber setting, plants were induced once with 100 ml 1% ethanol (root drenching) and invertase activity determined in tubers. The left panel shows invertase activity prior to (0) and after (1) ethanol induction visualised after SDS-PAGE. An untransformed wild type was used as a control and compared against independent transgenic lines 2, 3, 4, 5, 7 and 13 (see FIG. 16).

FIG. 17 shows the carbohydrate content of potato tubers two months after initial induction. Pat::cwINV, transgenic plants expressing yeast invertase were placed under control of the tuber-specific B33 patatin promoter (independent transgenic lines 3, 33 and 41). SC12 (Pat:: Alc:cwINV) transgenic plants (independent transgenic lines 2, 5, 7 and 13) are ethanol inducible. Tuber-specific expression of cell wall invertase is caused via tuber-specific expression of the alcR protein mediated by the B33 promoter.

Transgenic potato plants were propagated in tissue culture and transferred into the greenhouse. Ethanol induction occurred at three different development stages. $1^{st}$ induction, 25 days after transfer, $2^{nd}$ induction 32 days after transfer and a $3^{rd}$ induction 39 days after transfer. 10 plants from each genotype were used for each induction experiments. Initial induction occurred via root drenching. Due to the induction procedure plants induced after 25 days were vapour induced 32 and 39 days after transfer. Plants induced 32 days after transfer were induced a second time, whereas, plants induced 39 days after transfer were induced only once (see FIG. 18).

Other modifications of the present invention will be apparent to those skilled in the art without departing from the scope of the invention.

The invention claimed is:

1. A method of increasing the yield of a plant comprising:
   a. transforming a plant with a DNA construct comprising one or more DNA sequence(s) coding for invertase operably linked to an alcA promoter and optionally operably linked to a transcription terminator; and a DNA sequence encoding the alcR regulatory protein operably linked to a tissue specific or constitutive promoter; and
   b. controlling the level, time and spatial location of expression of said DNA sequence(s) from said inducible promoter region by application of an external chemical inducer comprising ethanol whereby the yield of said transgenic plant is increased.

2. Plant tissue transformed with a DNA construct according to claim 1.

3. Plants regenerated from plant tissue according to claim 2.

4. The method of increasing the yield of a plant according to claim 1 wherein said tissue specific promoter is a tuber specific promoter.

5. The method of increasing the yield of a plant according to claim 4, wherein said tuber specific promoter is a patatin promoter.

6. The method of increasing the yield of a plant according to claim 4, wherein said tuber specific promoter comprises −1512 to +14 of the patatin gene B33.

7. The method of increasing the yield of a plant according to claim 1, wherein said plant is a tobacco plant.

8. The method of increasing the yield of a plant according to claim 1, wherein said plant is a potato plant.

9. The method of increasing the yield of a plant according to claim 8, wherein said tissue specific promoter is a tuber specific promoter.

\* \* \* \* \*